(12) United States Patent
Shick et al.

(10) Patent No.: US 6,257,231 B1
(45) Date of Patent: Jul. 10, 2001

(54) AEROSOL ENHANCEMENT

(75) Inventors: John Shick, Jamesville; David Malys, Holland, both of NY (US); Jack Parco, Toledo, OH (US)

(73) Assignee: Ferraris Medical, Inc., Orchard Park, NY (US)

( * ) Notice: Subject to any disclaimer, the term of this patent is extended or adjusted under 35 U.S.C. 154(b) by 0 days.

(21) Appl. No.: 09/205,279

(22) Filed: Dec. 3, 1998

(51) Int. Cl.[7] .................................................. A61M 15/00
(52) U.S. Cl. ............................... 128/200.14; 128/200.18; 128/200.22
(58) Field of Search ...................... 128/200.14, 200.18, 128/200.23, 203.12, 203.15, 200.19, 200.22

(56) References Cited

U.S. PATENT DOCUMENTS

| | | | |
|---|---|---|---|
| 3,097,645 | * 7/1963 | Lester | 128/200.18 |
| 4,470,412 | * 9/1984 | Nowacki et al. | 128/200.18 |
| 4,690,332 | * 9/1987 | Hughes | 239/338 |
| 4,702,415 | * 10/1987 | Huges | 239/8 |
| 4,706,663 | * 11/1987 | Makiej | 128/200.18 |
| 4,953,545 | * 9/1990 | McCarty | 128/200.23 |
| 5,301,663 | * 4/1994 | Small, Jr. | 128/200.18 |
| 5,320,094 | * 6/1994 | Laube et al. | 128/203.12 |
| 5,415,162 | * 5/1995 | Casper et al. | 128/203.12 |
| 5,788,665 | * 9/1998 | Sekins | 604/19 |
| 5,791,340 | * 8/1998 | Schleufe et al. | 128/203.28 |
| 5,842,467 | * 12/1998 | Greco | 128/200.23 |
| 5,848,588 | * 12/1998 | Foley et al. | 128/200.23 |
| 5,899,201 | * 5/1999 | Schultz et al. | 128/203.23 |
| 5,954,047 | * 9/1999 | Armer et al. | 128/200.23 |

* cited by examiner

Primary Examiner—John G. Weiss
Assistant Examiner—V. Srivastava
(74) Attorney, Agent, or Firm—George E. Kersey, Esq

(57) ABSTRACT

Method and apparatus for an aerosol chamber having an input opening and an output opening with back pressure created in the chamber by an apertured barrier, such as a disk having a plurality of concentric and circumferentially disposed sets of openings to reduce the size of particles applied at the input opening before leaving the output opening, which is of lesser diameter than the input opening and extends to the input opening by an arcuate surface of revolution that serves to redirect interiorly of the chamber aerosol particles that have entered the chamber and reached the surface of revolution.

9 Claims, 10 Drawing Sheets

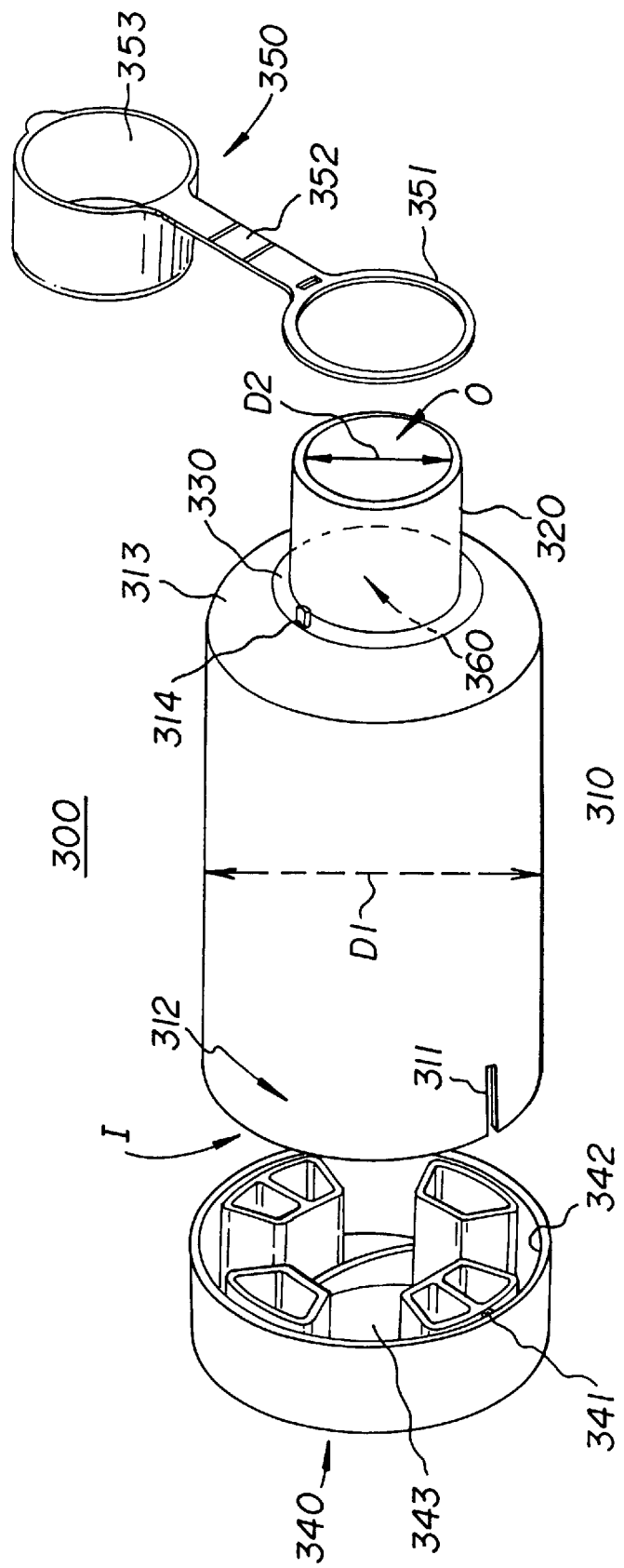

AEROSOL ENHANCEMENT

This invention relates to aerosol enhancement during fluid flow, and more particularly to the enhancement of therapeutic aerosols.

BACKGROUND OF THE INVENTION

Therapeutic aerosols, which are colloidal solutions dispensed in the form of a mist, are widely used in medical procedures. For example, the discharges from inhalation devices such Metered Dose Inhalers (MDI's) are used to deliver medications which will desensitise or dilate the bronchial passages which permit air movement from the trachea to the lungs. It often is necessary to relieve breathing difficulties associated with a variety of disorders by delivering a measured amount of medication to the site of breathing difficulty.

While oral and intravenous methods can be used inhalation therapy using MDI's has numerous advantages. The therapeutic effect is a more rapid, and a reduced amount of medication usually suffices. In addition, there can be a lower incidence of systemic side effects.

In order to operate suitably as a bronchodilator, or expander of the bronchial passages, an MDI system must ensure that sufficient medication reaches the lungs. This is accomplished by having the colloidal suspension forming an aerosol spray released by an MDI take the form of powder or liquid encapsulated by droplets of propellant.

Since the propellant droplets containing the medicament particles are pressurized, they have an initially rapid discharge velocity. In addition, where the aerosol particles are large and the flow rate is rapid, surface forces tend to agglomerate or increase the sizes of the droplets and particles. Where the droplets are large, much of the medication impacts the oropharynx, which is the central portion of the pharynx between the soft palate and the upper portion of the epiglottis, instead of the bronchial passageways which extend from the trachea below the epiglottis.

The sensory effect of oropharyngeal impact may be deceptive and lead a patient to believe erroneously that suitable medication has been achieved, although the desired bronchial site has not been fully medicated with a required dosage. In addition, the localization of medication in the oropharynx can produce adverse side effects when certain aerosols are used, such as those containing corticosteroids. The undesired side effects can include oropharyngeal candidiasis, which is a mucus infection, or dysphonia, which results in hoarseness and difficulty in speaking.

In order to have proper disposition of aerosolized medication in the lungs, rather than in the mouth, it is necessary to coordinate the aerosol discharge by inhaling slowly and deeply, and by using a breath-hold technique upon the completion of inhalation. Otherwise, a reduced amount of aerosol medicament particles are deposited in the lungs with reduced therapeutic effect.

In various attempts to ensure sufficient aerosolized drug deposits in the lungs, several extension devices have been provided for attachment to MDI's. These extension devices have the objective of permitting inhalation of only smaller and slower moving particles.

One such extension device is disclosed in Makiej, U.S. Pat. No. 4,706,663 ('663), issued Nov. 17, 1987 for PARTICLE CATCHER FOR INHALATION DEVICES, in which a particle catcher is placed directly across the inhalation mouth- or nasalpiece opening. The particle catcher is an injection-molded plastic screen formed integrally with, and along the cross section of one end of a flexible support tube. The injection molded plastic screen includes a structural array of interconnecting elements and openings which are of a prescribed size to limit the size of particles and droplets which can pass through the screen.

Activation of the MDI aerosol canister discharges a medicinal spray in the direction of the screen where the aerosolized medication communicates with the interconnecting elements and openings of the screen. Oropharyngeal impaction is said to be reduced because of screen permeation, accompanied by increased bronchial deposition.

However, the combination of extension devices with MDI's can be cumbersome and bulky, often taking the form of multi-piece chambers, and cone shaped spacers or collapsible bags, which can range in length to 25 centimeters (10 inches) and in volume to 1000 cubic centimeters (61 cubic inches).

Although size reductions have been attempted by some collapsible extension devices, they do not deliver the desired medication unless fully extended.

Accordingly, it is an object of the invention to facilitate aerosol medication, particularly in conjunction with metered dose inhalers (MDI's).

Another object is to achieve enhanced medication using a small, portable metered-dose inhaler extension which is easy to use and yet can effectively discharge medicinal aerosols.

Still another object of the invention is to avoid the need for positioning a screen at the cross-sectional inhalation end of devices. A related object is to avoid the need for screen apertures of a prescribed size in order to prevent throughpassage of unsuitable droplets.

A further object of the invention is to avoid the need for a particle catcher in order to reduce the size and velocity of aerosol droplets discharged from inhalation devices. Yet another object is to reduce oropharyngeal impaction while increasing the deposition of aerosolized medicine in the bronchial passageways.

Yet another object is to provide an MDI extension which is small, unobtrusive, simple and inexpensive to fabricate.

A still further object of the invention is to provide inhalation therapy for less coordinated patients that is comparable to the therapeutic achieved by patients with good inhalation skills.

SUMMARY OF THE INVENTION

In accomplishing the foregoing related objects the invention provides an aerosol extension chamber having an apertured barrier between input and output openings in order to create back pressure against particles applied at the input opening to assist in size reduction before the particles exit at the output opening.

The apertured barrier advantageously is located in the chamber at a position of transition between the input opening and the output opening.

In accordance with one aspect of the invention, the apertured barrier is a disk having a plurality of concentric sets of openings which are circumferentially disposed. A circular opening can be located at the center of the disk.

In accordance with another aspect of the invention the aerosol extension chamber has an input end cap at the input opening of the chamber for receiving a metered aerosol source which has an outlet that is insertable into the end cap through an opening having parallel linear sides bounded by upper and lower curved segments. The parallel sides can extend into the chamber to stabilize the insertion of the metered source outlet and limit the extent to which the aerosol from the source is direct off-axis into the chamber. Outward projections from the input end cap can control the spacing relative to the aerosol source when the extension chamber is positioned on the outlet for the source.

The aerosol chamber of the invention can have its housing extended to a lesser diameter by an arcuate surface of revolution, with the arcuate surface serving to redirect interiorally of the chamber aerosol particles that have entered the chamber and reached the surface of revolution.

The apertured aerosol barrier advantageously is formed with a plurality of sets of circular openings disposed circumferentially at a plurality of different radii and is positioned advantageously in the chamber at a transition from the surface of revolution to the lesser diameter. The circular openings can be of different sizes in different circumferential dispositions, and the openings of a circumferential disposition at a first radius can be smaller than the circumferential openings at a greater radius. A circular opening in the barrier can be positioned to coincide with the central axis of the chamber.

In a method of the invention for enhancing the reduction in size of aerosol particles, the steps can include (a) applying an aerosol spray to a chamber having an input opening and an output opening; and (b) creating back pressure curvature redirection in the chamber against the particles of an aerosol spray applied at the input opening in order to reduce the size of particles leaving the output opening.

The method can further include the step of applying the aerosol spray to a stabilized opening of the chamber in order to cause the spray to enter the chamber along its central longitudinal axis. The opening of the chamber can be stabilized by extending the side walls of the opening into the chamber.

The method also can include the step of removing a cap covering the output opening and placing the cap in a temporary retention position along the side of the chamber in a position that avoids interference with the placement of the chamber into the mouth of a user.

In accordance with another aspect of the invention, a one-way valve can be positioned within the extension chamber so that only inhalation at the output opening of the camber, and exhalation is prevented. The one-way valve can take the form of a flap overlying an interiorly located support.

BRIEF DESCRIPTION OF THE DRAWINGS

Other aspects and advantages of the invention will become apparent after considering several illustrative embodiments taken in conjunction with the drawings, in which:

FIG. 2A is a perspective view of the extension chamber of FIGS. 1A and 1B with an input end cap separated from the chamber housing and an output end cap shown removed from the outlet end of the chamber housing.

DETAILED DESCRIPTION

Figure 1A:
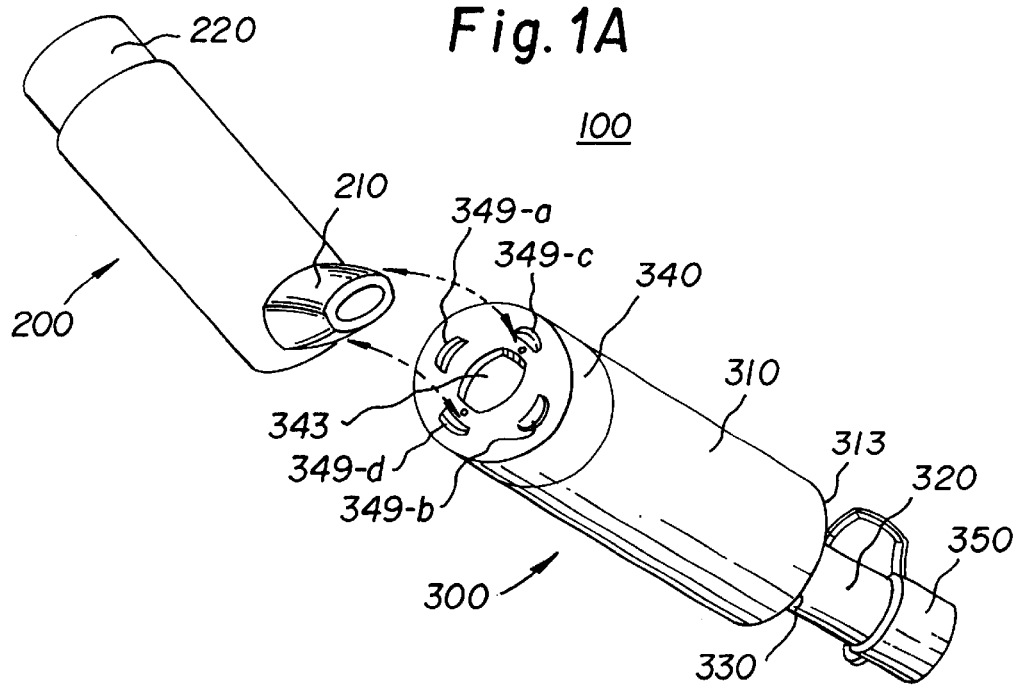
FIG. 1A is a perspective view of aerosol extension chamber in accordance with the invention preparatory to being positioned on an MDI aerosol source.

With reference to the drawings, FIG. 1A shows a medication system 100 of the invention formed by an aerosol extension chamber 300 preparatory to being positioned on a Metered Dosage Inhalation (MDI) aerosol source 200.

Figure 1B:
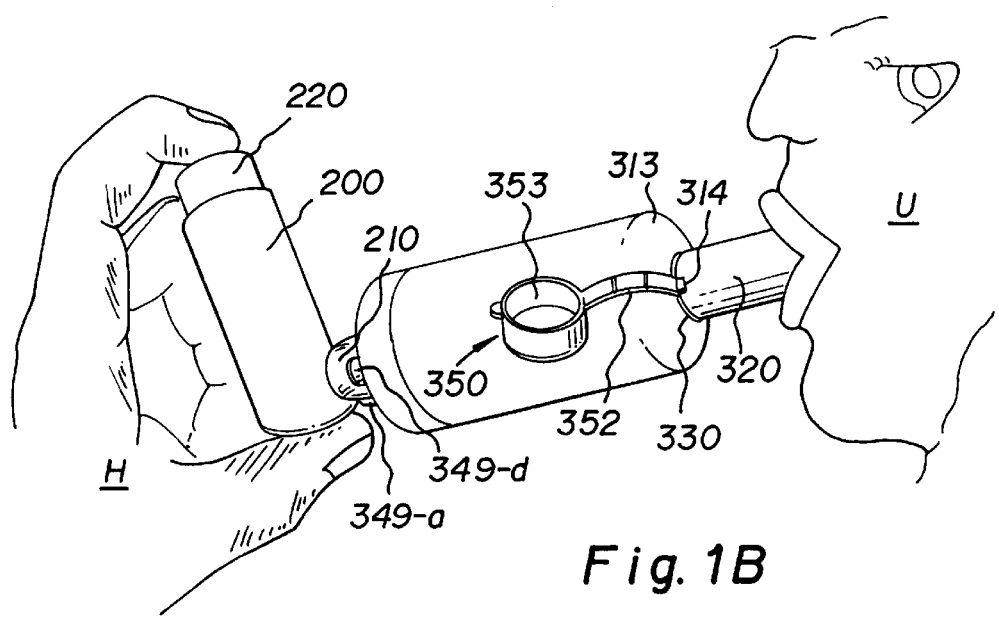
FIG. 1B is a partial perspective view showing the extension chamber of FIG. 1A mounted on the aerosol source and operated by the hand of a user to apply small particle medication through the mouth of the user.

In FIG. 1B, the extension chamber 300 has been positioned on the output end 210 of the source 200, and the outlet cap 350 of the chamber 300 has been removed to allow placement of the chamber outlet extension 320 in the mouth of a user U whose hand H is shown depressing a canister 220 which has been inserted into the body 230 of the dispenser 200 to apply aerosol medication.

The extension chamber 300 of the invention is used in inhalation therapy to reduce the size and velocity of aerosol particles and droplets sprayed from the dispenser 200, so that an increased amount of dispensed medication is deposited in the respiratory tract of a patient, instead of in the oropharynx above the large central airways of the lungs.

The therapeutic efficiency of aerosol therapy is dependent upon ensuring that a sufficient amount of inhaled medication reaches the lungs. The extension chamber 300 of the invention achieves an enhanced therapeutic effect by creating back pressure within the chamber using a barrier grid with apertures of varying size; also by using a curved shoulder of the chamber to direct larger particles of the aerosol back into the chamber for size reduction, and by using a modified inlet for the chamber, supporting the aerosol source 200 to maintain centralized output flow into the chamber 300.

An important aspect of the invention, as described below, is the use of a grid with multiple circular openings in order to optimize the performance of the chamber.

As shown in FIG. 2A, the chamber 300 is formed by three sections. A main housing 310 is affixed to an output extension 320 at the position 330 of transition from the maximum diameter D1 of the housing 310 to the reduced diameter D2 of the output extension 320. At the transition 330 there is an apertured barrier 360 (not visible in FIG. 2A) shown in detail in FIGS. 3A and 3B and described below.

Before being applied to the source 200, the extension chamber 300 has the input end cap 340 secured to the input end of the main housing 310, being guided into position by an alignment groove 311 at the skirt 312 of the housing 310. The groove 311 engages a rib 341-r on the interior wall 342 of the end cap 340 to assure proper positioning of the cap 340 on the skirt 312, as shown in FIG. 2B.

Figure 2B:
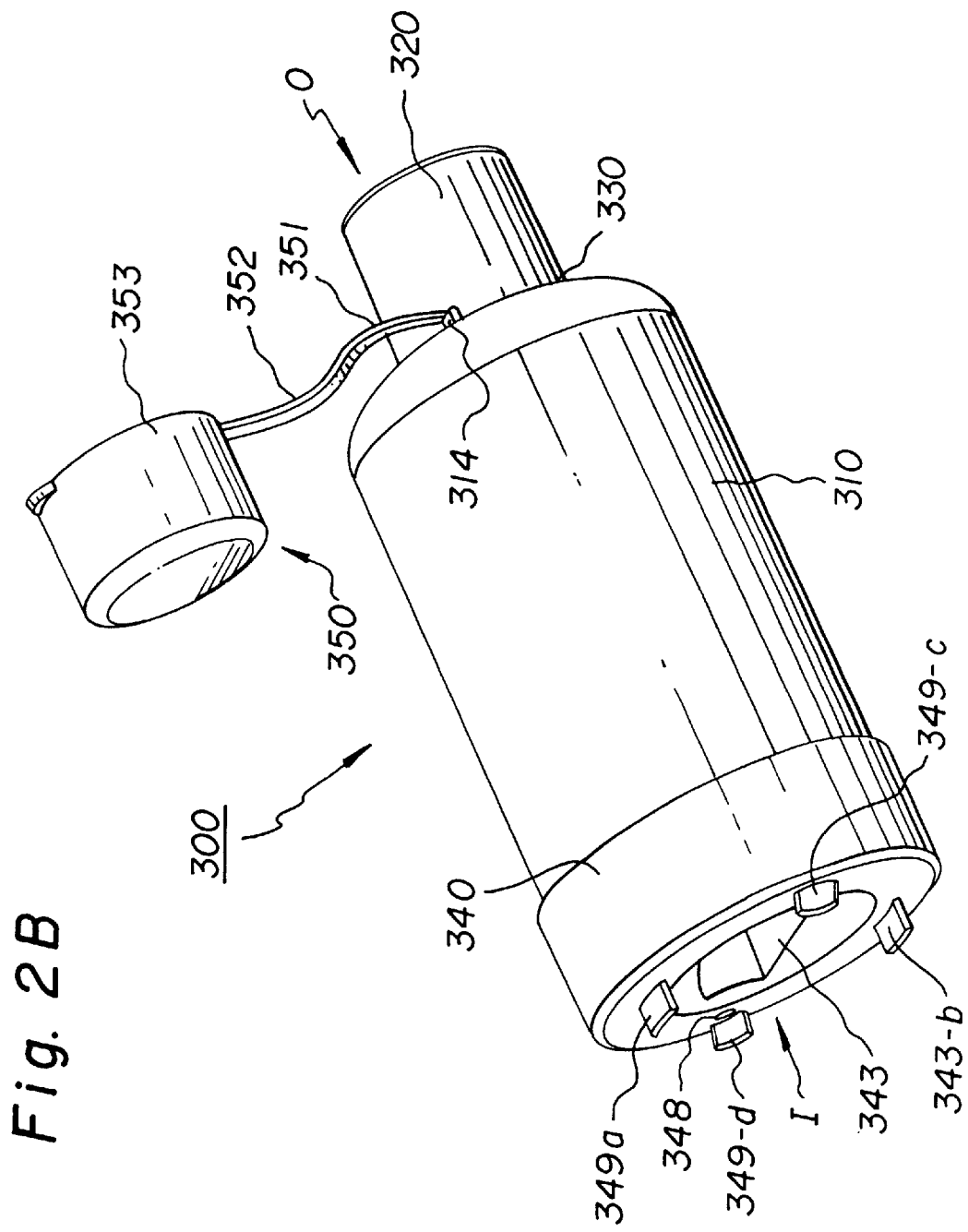
FIG. 2B is a perspective view of FIG. 2A showing the input end cap positioned on the chamber housing and the output end cap removed from the output opening, but tethered to the output end of the chamber housing.

In addition, the outlet end cap 350 has the ring 351 positioned on the extension 320 as shown in FIG. 2B on a support hook 314 at an opening 354, so that when the cup 353 is removed from the extension 320, as shown in FIG. 2B, the cup 353 will hang from the tether 352 at the side of the housing 310 and not interfere with user U of FIG. 1B.

Figure 3A:
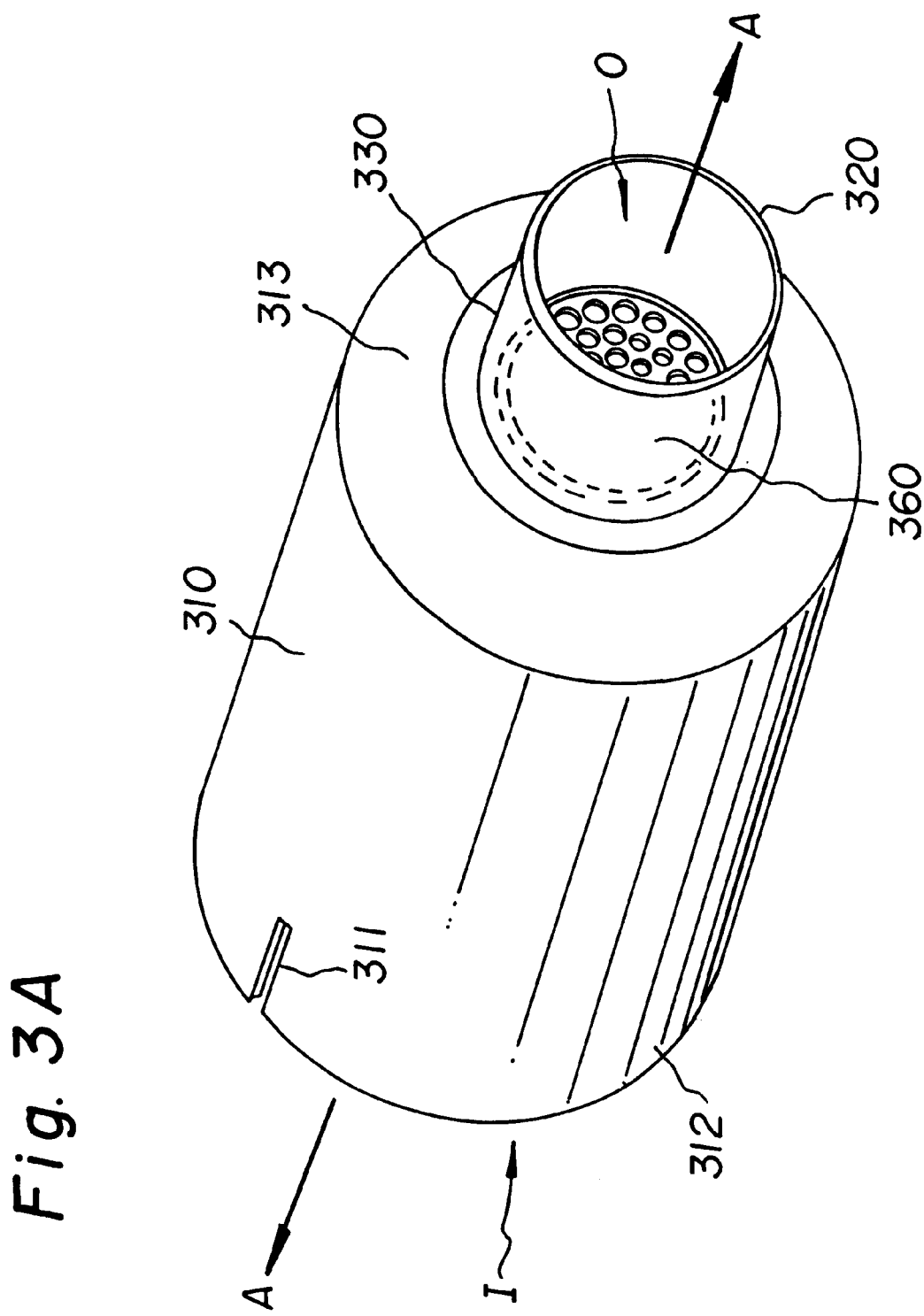
FIG. 3A is a perspective view of the chamber housing of Fig. 2A showing an apertured barrier positioned at the curved transition from the inlet end to the outlet end.
Figure 3B:
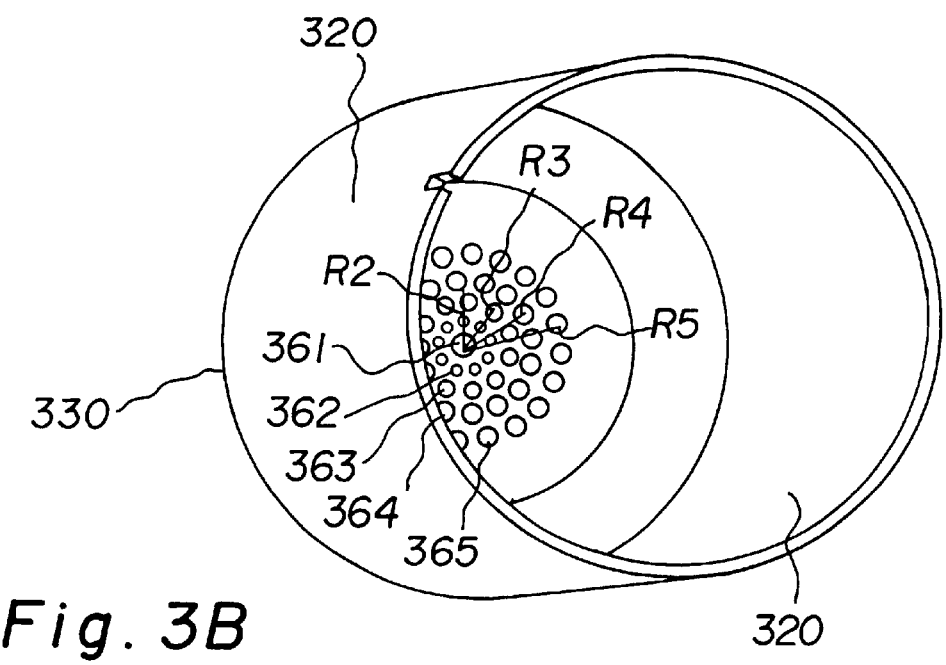
FIG. 3B is an enlarged perspective view showing the input end of the chamber housing and the circumferentially disposed circular apertures of the barrier at the output end of the invention.
Figure 4A:
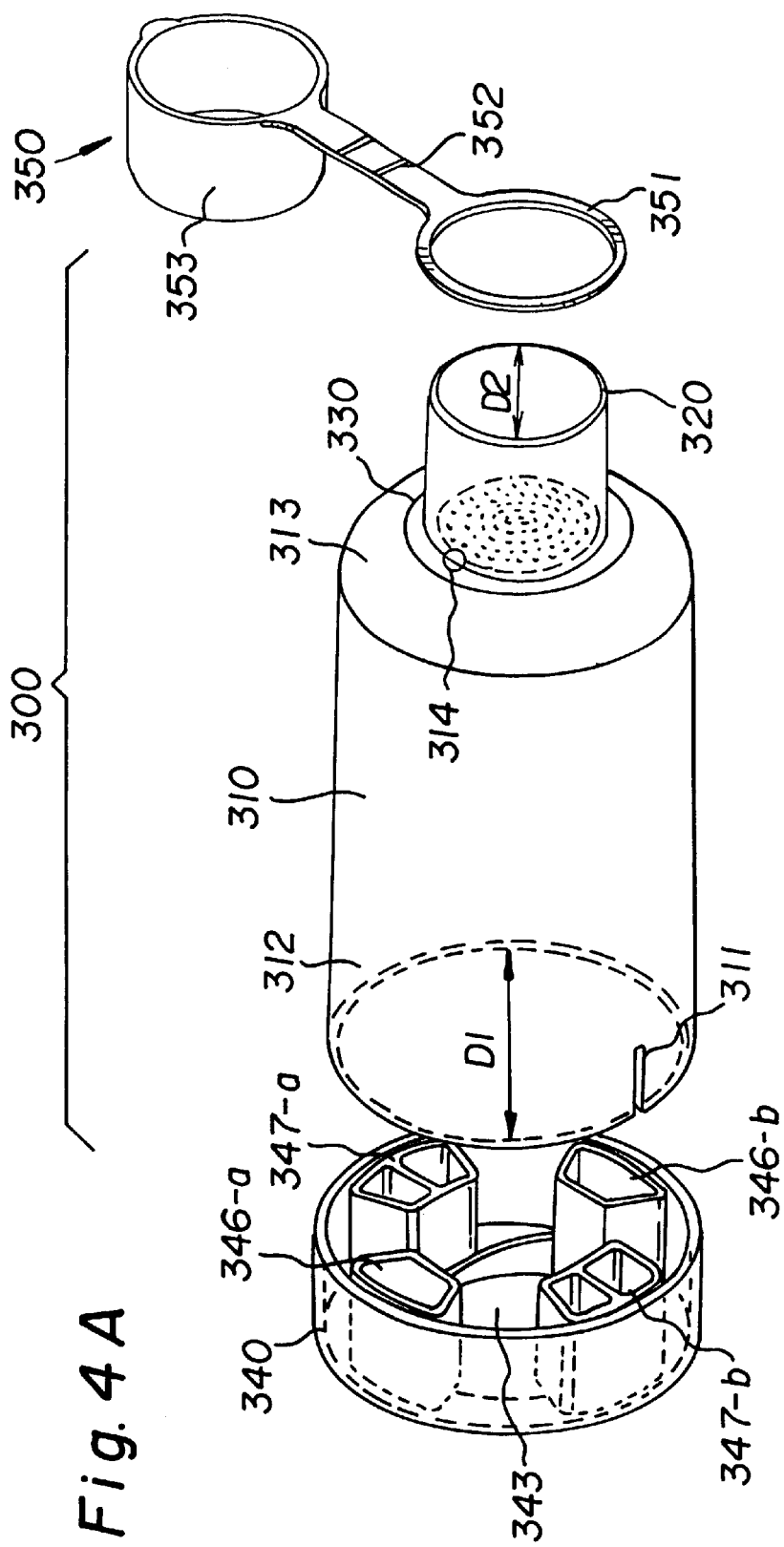
FIG. 4A is a view of FIG. 2A, partially in phantom, showing the wall thickness of the chamber housing, the internal structure of the input end cap and the structure of the output end cap which can cover the breathing end of the chamber housing.
Figure 4B:
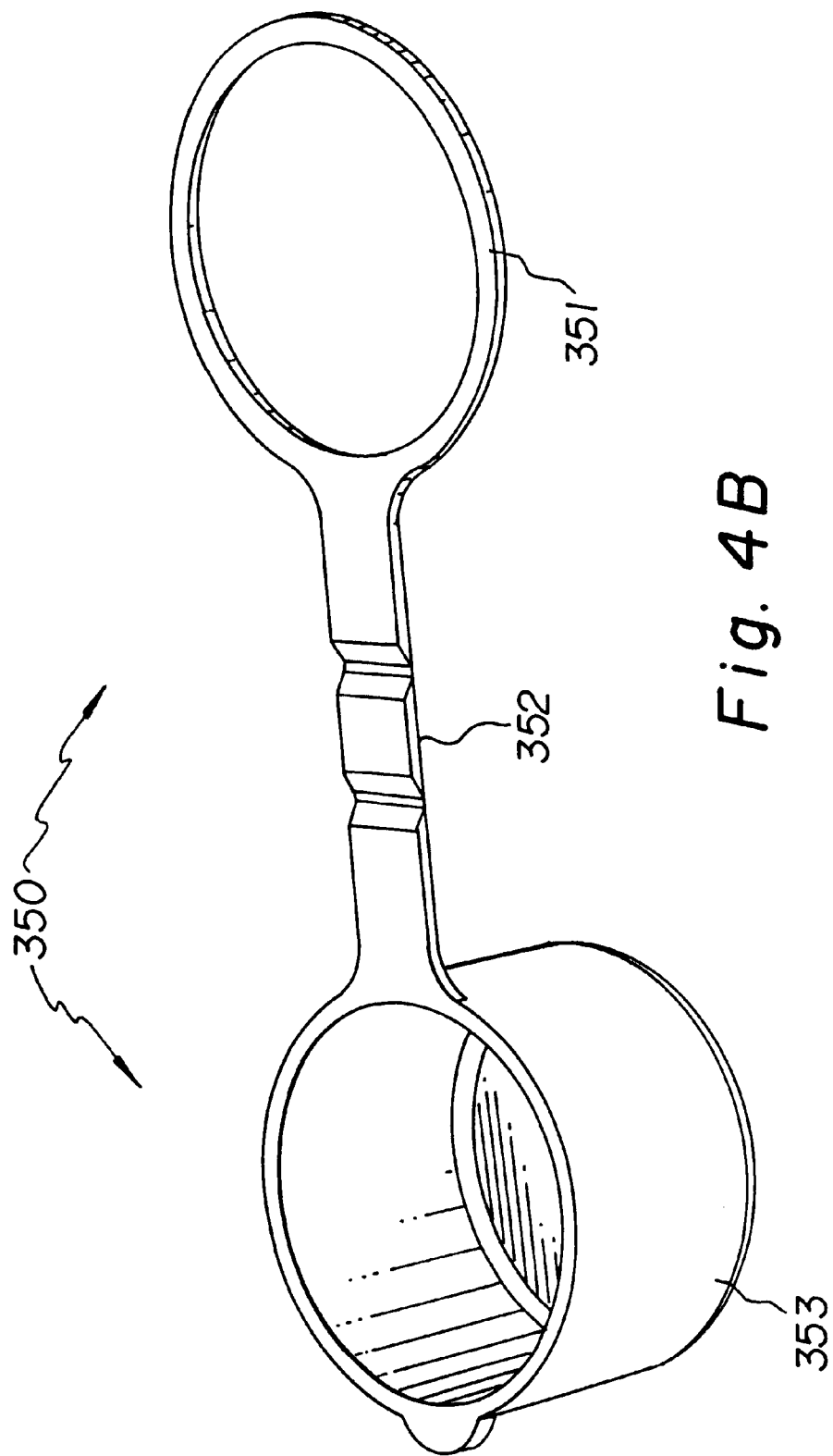
FIG. 4B is an enlarged view of the end cap of the invention with its tether connection to a fastening ring by which the end cap is secured to the chamber housing.

As seen in FIG. 3A, the barrier disk 360 is formed by a circumferential set of apertures at different radii with a central aperture 361 (FIG. 3B) coincident with the axis A of the housing 310, illustratively having a diameter of 0.093 inches.

The central opening 361 is surrounded by four sets 362 through 365 of circumferential openings, with the openings of each different set having a different diameter. Thus, the set 362 is formed by nine openings at a radius R2, with each opening having a diameter of approximately 0.045 inches. The next set 363, at a radius R3 includes eleven openings each having a diameter of approximately 0.065 inches. A fourth set 364, at a radius R4 includes sixteen apertures each having a diameter of approximately 0.070 inches. The final set 365, at a radius R5 includes 20 openings each with a diameter of approximately 0.080 inches.

It will be understood that the selected diameters have been found to achieve improved performance for the aerosol chamber 300, but it will be appreciated that other diameters and openings may also be used.

Ordinarily, the large droplets and agglomerations of droplets formed upon discharge from the source 200 are dispersed uniformly through the spray medium. In some instances, however, large droplets and agglomerations of droplets become entrained. This effect is reduced due to the construction of the chamber 300.

The chamber housing 310 with the extension 320 may be of any medically safe resin or polymer and be formed by injection molding so that a single-piece, homogeneous chamber is produced having the barrier disk 360 integrally formed with, and extending across the interior of the chamber at the transition 330 between the input section 310 and the output section 320.

The chamber 300 is preferably made from a chemically resistant plastic. The housing 310 desirably is a copolyester, while the inlet 340 is desirably "santoprene" (thermoelastic) or polyvinyl chloride (PVC). Flexible material is advantageous for the inlet 340 since that promotes slidable mounting upon, and the support of, a variety of geometrically shaped inhalation mouthpieces.

Prior to receiving a dosage of the prescribed medication, the single-piece homogeneous extension chamber 300 is mounted upon the mouthpiece 210 of the inhaler 200 as shown in FIGS. 1A and 1B.

Figure 5A:
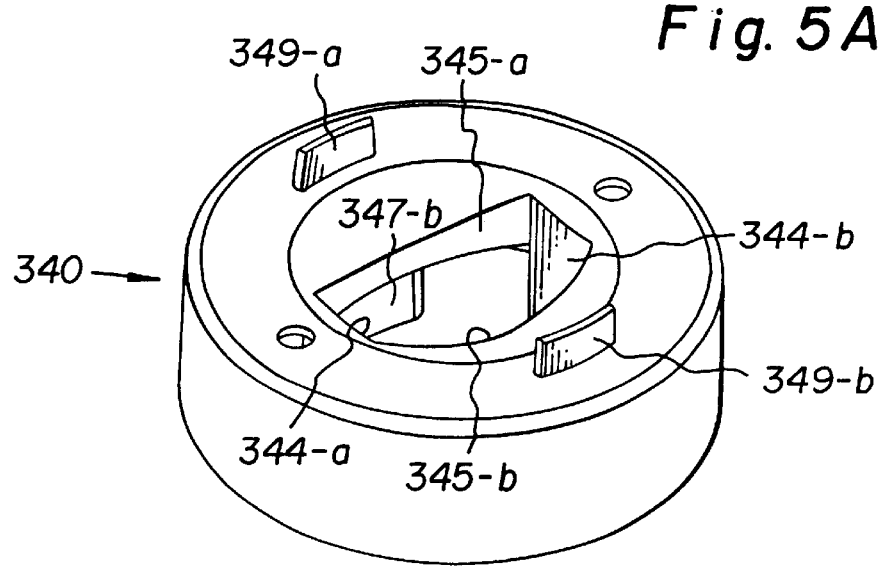
FIG. 5A is an enlarged view of the exterior of the input cap for the chamber housing of the invention.
Figure 5B:
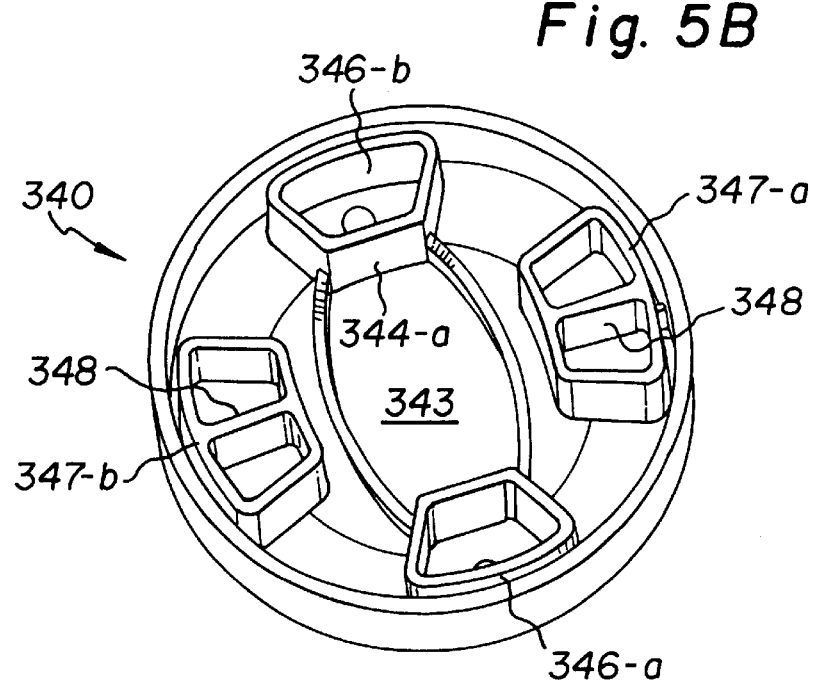
FIG. 5B is an enlarged view showing the interior of the input cap of FIG. 5A.

The open end 343 of the input cap 340, opposite the apertured disk 360 is positioned on the mouthpiece 210 of FIG. 1A. In order to ensure that the chamber 300 is fixedly maintained in position during the inhalation process, the opening 343. as shown in FIGS. 5A and 5B, is proportioned to have side walls 344-a and b, and 345-a and b that correspond to the configuration of the mouthpiece 210. The end cap 340 has a circular recess 341 to accommodate circular mouthpieces.

The input cap 340 also has air entrainment apertures 348 to prevent restriction of end user inhalation flow rate.

In addition, in order to avoid off-axis discharge into the chamber 300, the opposed, parallel and linear side walls 344-a and 344-b extend into the interior of the housing 310. Similarly the opposed arc segments 345-a and 345-b also extend into the interior of the housing 310.

Projections 349-a and 349-b in FIG. 5A control the distance between the end cap 340 and the body of the source, such as a metered-dose inhaler. Some sources have the 90 degree configuration as shown in FIGS. 1A and 1B where the mouthpiece 210 extends at a right angle with respect to the housing 230 of the source 200. However, other sources cut the angle between the housing 230 and the mouthpiece 210 to 45 degrees so that when the source is inserted there is a danger that the mouthpiece will have an upward tilt that directs the input flow off axis. This possibility is avoided by the invention through the use of projections 349-a and 349-b which prevent the mouthpiece from adopting an upward tilt.

Unlike the prior art, where the source body can go to the end cap, the projections 349-a and 349-b of the invention increase the internal distance of the source 200 from the apertured disk 360, thus increasing the distance for therapeutic aerosol formation.

The additional projections or supports 349-c and 349-d help to prevent the occlusion of air entrainment apertures 348.

Further stabilization for the mounting of the chamber 300 on the source 200 is provided by the internal structure of the end cap 340 shown in FIG. 5B, where the extended side walls 344-a and 344-b are supported by trapezoidal buffers 346-a and 346-b. Other trapezoidal buffers 347-a and 347-b join the respective arcuate walls 345-a and 345-b, with each buffer 347-a and 347-b having an internal reinforcement rib 347-r.

Of course, the inhalation device upon which the extension chamber 300 may be mounted is not simply limited to a metered-dose inhaler but may also include other inhalation devices, such as dry-powder inhalers or nebulizers, or other similar devices.

Subseauent to activation of the aerosol canister 220, a metered dose of medication is dispensed from the mouthpiece 210. As the therapeutic aerosol communicates with the extension chamber 300, back pressure is applied by the internal disk 360, together with a redirection of large droplets by the housing curvature 313 at the transition position 330, so that a stream of appropriately fine particles can reach the lungs of the user. The larger particles and agglomerations redirected into the chamber are either deposited or reduced in size and joined to the outgoing stream.

As noted earlier, in order to have proper disposition of aerolosized medication in the lungs, rather than in the mouth, it is necessary to coordinate the aerosol discharge by inhaling slowly and deeply, and by using a breath-hold technique upon the completion of inhalation. Otherwise, a reduced amount of aerosol medicament particles is deposited in the lungs with reduced therapeutic effect.

Where patients do not have good inhalation skills, the invention provides inhalation therapy for less coordinated patients, comparable to the therapeutic achieved by patients with good inhalation skills, by adapting the extension chamber 300 to have a one-way valve and valve support at the transition position 330.

Figure 6A:
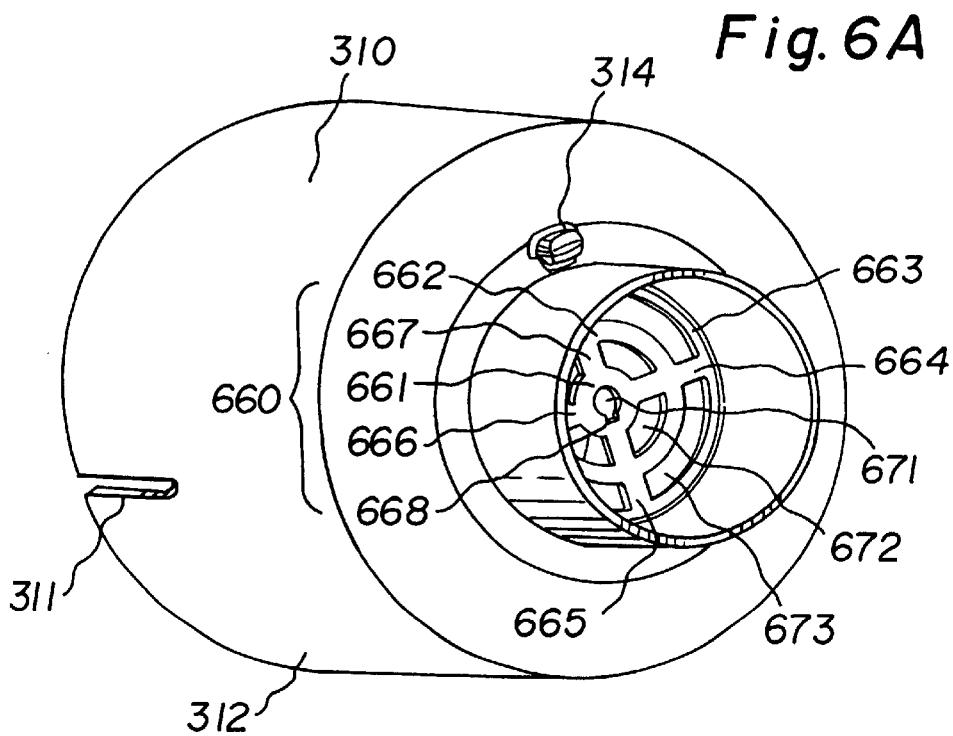
FIGS. 6A and 6B are partial perspective views of a modification of the chamber of FIG. 2A showing a support of the invention for an umbrella valve shown in FIG. 6C to allow only inhalation operation of the chamber of the invention.
Figure 6B:
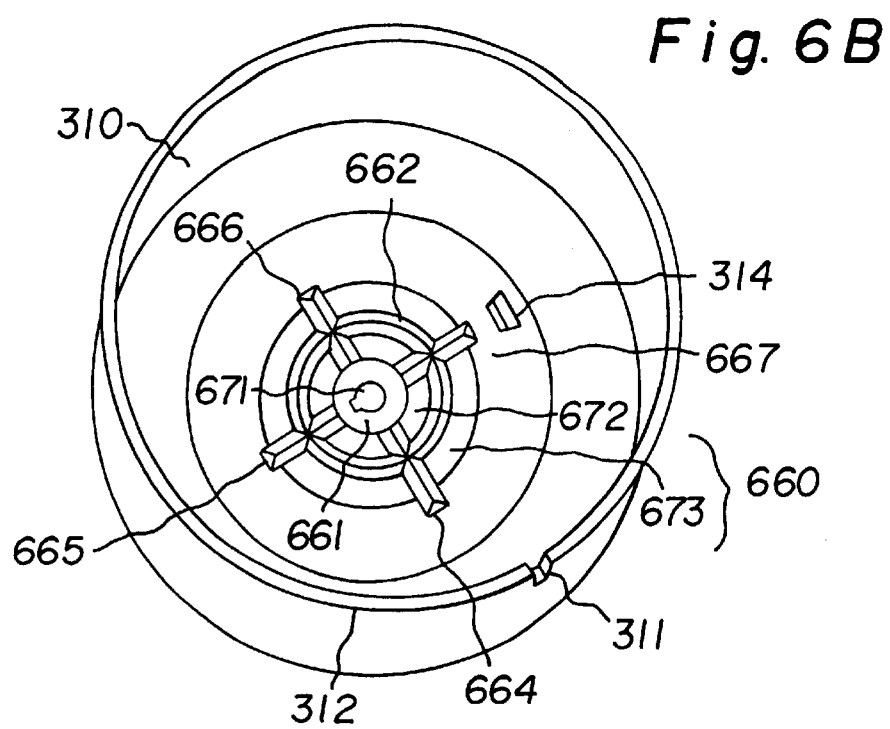
Figure 6C:
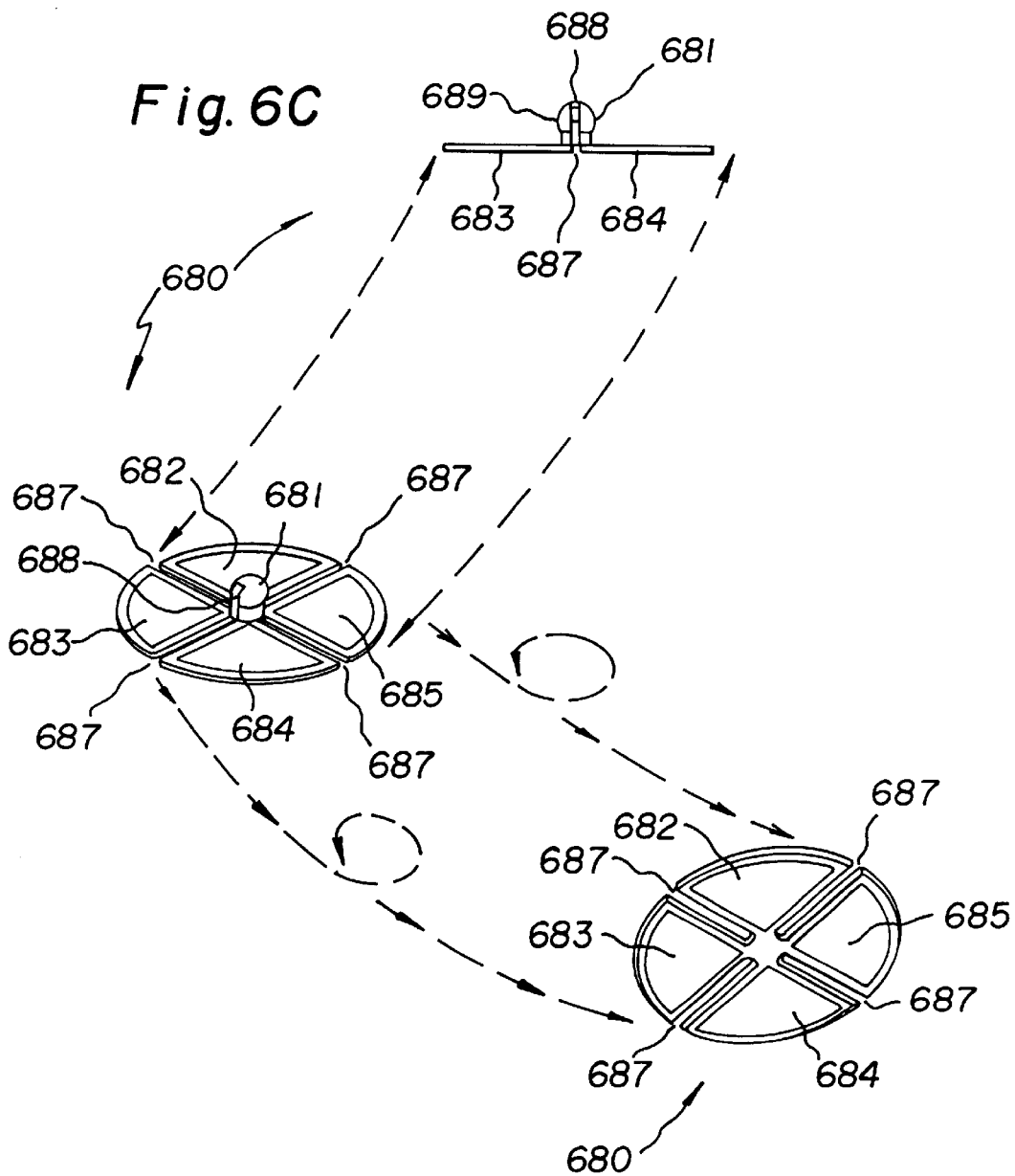

One way of accomplishing this result is illustrated in FIGS. 6A–6C. In FIG. 6A the barrier disk 360 of FIG. 3A has been replaced by a valve support 660 on which is mounted the umbrella valve 680 shown in FIG. 6C. The valve support 660 is formed by concentric rings 661, 662 and 663 with radial arms 664, 665, 666 and 667 extending from the inner ring 661, which has a positional notch 668.

In order to mount the umbrella valve 680 on the support 660, the prong 681 shown in FIG. 6C is inserted into the central opening 671 of the ring 661. This causes the butterfly segments 682–685 to lie upon the concentric rings and radial arms of the support 660. It will be noted that the rings 661–663 include sector openings 671 and 672 in order to allow aerosol medication to pass through the output opening 320 and to reduce adherence of the segments 682–685 on the support 660 during inhalation.

The umbrella valve 680 of FIG. 6C is shown having its prong 681 with an axial outer rib 688 to properly position butterfly segment 682–685 of the umbrella valve valve 680 onto the support. In order to promote retention of the inserted umbrella valve 680 on the support 660, the prong 681 has a bulbous end 689. The segments 682–685 are separated by grooves 684 which extend from the prong 681 to the circumference of the segments 682–685. Grooves 687 allow each segment of the umbrella valve to move separately from one another.

The structure of the concentric rings 661, 662 and 663, and the radial arms 664, 665, 666 and 667 extending from the inner ring 661, is shown in FIG. 6B as viewed from the insert end of the chamber with the end cap 340 removed.

While the rings and arms of FIG. 6A are flat to accommodate the umbrella valve 680, that structure in FIG. 6B has a triangular cross-section in order to promote through-flow and reduce aerosol impaction, while increasing the structural integrity of the support 660 for the umbrella valve 680 on its flat side.

It will be appreciated that although the one-way valve 600 of FIG. 6 takes the form of a umbrella valve 680 covering a support 660, other forms of one-way valve may be employed.

The serves as a baffle to force the impaction of high velocity non-therapeutic particles that would otherwise end in the mouth.

It also will be appreciated that the foregoing embodiments are merely illustrative and that other modifications and adaptations of the invention will be apparent to those of ordinary skill in the art.

What is claim:

1. Apparatus comprising a cylindrical aerosol chamber having an input opening and a circular output opening; and
   an apertured barrier means positioned in the chamber having the same diameter as said output opening for creating back pressure against aerosol particles applied at the input opening of the chamber in order to reduce the aerosol particle sizes before exiting the output opening; and
   wherein said apertured barrier means has circular openings of different sizes.

2. Apparatus as defined in claim 1 wherein said apertured barrier means comprises a disk having a plurality of concentric sets of different-sized openings which are circumferentially disposed.

3. Apparatus as defined in claim 1 further including a circular opening at the center of said apertured barrier means.

4. Apparatus as defined in claim 1 wherein said apertured barrier means has a lesser diameter than the diameter of said chamber.

5. Apparatus as defined in claim 1 wherein said aerosol chamber has an end cap at said input opening for receiving a metered source of aerosol.

6. Apparatus as defined in claim 5 wherein the end cap has parallel sides extending into the inlet opening of the chamber adapted for insertion of said metered source and to limit the extent of insertion of said metered source into the chamber for delivery of aerosol.

7. Apparatus as defined in claim 5 wherein the end cap has projections extending outwardly therefrom for limiting the distance of insertion of said metered source into the chamber when positioned thereon.

8. Apparatus as defined in claim 1 wherein the aerosol chamber has an input opening of prescribed diameter extending to the apertured barrier means having a diameter lesser than the diameter of the cylindrical chamber by an arcuate surface of revolution;
   whereby the arcuate surface of revolution serves to redirect interiorly aerosol particles to the apertured barrier means.

9. Apparatus as defined in claim 8 wherein the apertured barrier means creates back pressure against aerosol particles and is positioned in the chamber at a transition from the arcuate surface of revolution to the lesser diameter of the apertured barrier means.

* * * * *